(12) United States Patent
Murray et al.

(10) Patent No.: US 10,300,003 B2
(45) Date of Patent: May 28, 2019

(54) HAIR SHAPING COMPOSITION

(71) Applicant: Conopco, Inc., Englewood Cliffs, NJ (US)

(72) Inventors: Andrew Malcolm Murray, Neston (GB); Prem Kumar Cheyalazhagan Paul, Wirral (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 15/743,060

(22) PCT Filed: Jul. 15, 2016

(86) PCT No.: PCT/EP2016/066957
§ 371 (c)(1),
(2) Date: Jan. 9, 2018

(87) PCT Pub. No.: WO2017/013034
PCT Pub. Date: Jan. 26, 2017

(65) Prior Publication Data
US 2018/0185260 A1    Jul. 5, 2018

(30) Foreign Application Priority Data

Jul. 21, 2015 (EP) .................................. 15177614

(51) Int. Cl.
*A61Q 5/04* (2006.01)
*A61K 8/36* (2006.01)
*A61K 8/49* (2006.01)
*A61K 8/362* (2006.01)
*A61K 8/365* (2006.01)

(52) U.S. Cl.
CPC ............... *A61K 8/498* (2013.01); *A61K 8/36* (2013.01); *A61K 8/362* (2013.01); *A61K 8/365* (2013.01); *A61K 8/4973* (2013.01); *A61Q 5/04* (2013.01)

(58) Field of Classification Search
CPC ...................................................... A61Q 5/04
See application file for complete search history.

(56) References Cited

U.S. PATENT DOCUMENTS

2015/0305469 A1    10/2015    Paul

FOREIGN PATENT DOCUMENTS

| WO | WO0042978 | 7/2000 |
|---|---|---|
| WO | WO2005084623 | 9/2005 |
| WO | WO2011104282 | 9/2011 |
| WO | WO2012105985 | 8/2012 |
| WO | WO2013174690 | 11/2013 |
| WO | WO2014072645 | 5/2014 |
| WO | WO2015074846 | 5/2015 |

OTHER PUBLICATIONS

Search Report and Written Opinion in PCT2016066957, dated Sep. 30, 2016.
Search Report and Written Opinion in PCTEP2016066949, dated Sep. 13, 2016.
Search Report in EP15177612, dated Nov. 19, 2015.
Search Report in EP15177614, dated Dec. 3, 2015.
Written Opinion in EP15177614, dated Dec. 3, 2015.
Co-Pending Application, U.S. Appl. No. 15/743,029, filed Jan. 9, 2018.

*Primary Examiner* — Gina C Justice
(74) *Attorney, Agent, or Firm* — Foley & Lardner LLP

(57) ABSTRACT

The invention provides a hair shaping composition suitable for topical application to hair, the composition having a pH of 4 or less and comprising, in an aqueous continuous phase: (i) at least 0.5% (by weight based on the total weight of the composition) of one or more polyhydroxy acid lactones; (ii) at least 0.5% (by weight based on the total weight of the composition) of one or more aliphatic di- or tricarboxylic acids, and (iii) at least 0.1% (by weight based on the total weight of the composition) of glyoxylic acid or a salt or hydrate thereof.

11 Claims, No Drawings

HAIR SHAPING COMPOSITION

FIELD OF THE INVENTION

This invention relates to a hair shaping composition, and more particularly a hair shaping composition which does not require the breakage of hair disulfide bonds.

Background and Prior Art

Many people with naturally kinky, curly, or even wavy hair often desire to straighten their hair. Permanent hair straightening compositions that are on the market are based on chemical treatment of the hair in a two-step process using reducing agents to break hair disulfide bonds, followed by a neutralisation or oxidation step to re-establish new disulfide bonds in the desired configuration. Such systems have various negatives associated with them; in that the process itself is difficult to conduct, in many instances this straightening process is undertaken by a qualified hairdresser in a professional salon. Furthermore the straightening process damages the hair, has an unpleasant odour and can cause irritation to the scalp.

Surprisingly we have found that hair can be shaped without causing the chemical damage which is traditionally associated with permanent hair straightening processes involving breakage of the hair disulfide bonds.

Advantageously the method of the invention can be accomplished by a consumer without intervention of a professional hairdresser. Furthermore, hair shaped with the method of the invention remains shaped even after subsequent washing.

SUMMARY OF THE INVENTION

The present invention provides a hair shaping composition suitable for topical application to hair, the composition having a pH of 4 or less and comprising, in an aqueous continuous phase:
(i) at least 0.5% (by weight based on the total weight of the composition) of one or more polyhydroxy acid lactones;
(ii) at least 0.5% (by weight based on the total weight of the composition) of one or more aliphatic di- or tricarboxylic acids or salts or hydrates thereof, and
(iii) at least 0.1% (by weight based on the total weight of the composition) of glyoxylic acid or a salt or hydrate thereof.

The invention also provides a method for shaping hair which comprises the steps of treating the hair by topical application of a hair shaping composition as defined above, followed by mechanically shaping the treated hair.

DETAILED DESCRIPTION AND PREFERRED EMBODIMENTS

All molecular weights as used herein are weight average molecular weights, unless otherwise specified.

By "aqueous continuous phase" is meant a continuous phase which has water as its basis.

A hair shaping composition according to the invention will generally comprise at least 60%, preferably at least 70% and more preferably at least 80% water (by weight based on the total weight of the composition). Preferably, the composition comprises no more than 99% and more preferably no more than 98% water (by weight based on the total weight of the composition). Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

The hair shaping composition of the invention comprises, as component (i), one or more polyhydroxy acid lactones.

Polyhydroxy acid lactones for use in the invention are typically aliphatic compounds having at least two hydroxyl groups in the molecule and with a preferred molecular weight of between about 100 and about 300.

Preferred polyhydroxy acid lactones for use in the invention contain from 3 to 8 carbon atoms and from 2 to 8 hydroxyl groups, with at least two of the hydroxyl groups being respectively attached to two adjacent carbon atoms of the molecule.

Illustrative examples of such materials include:
(a) Aldonic Acid Lactones

Aldonic acids are polyhydroxy acids resulting from oxidation of the aldehyde group of an aldose to a carboxylic acid group, and the acid of which can be represented by the following general formula:

$$H(CHOH)_nCH(OH)COOH$$

where n is an integer from 1 to 6.

The aldonic acids can exist as stereoisomers as D, L and DL or R, S and RS forms. The aldonic acids form intramolecular lactones by removing one mole of water between the carboxyl group and one hydroxyl group.

The following are representative aldonic acid lactones:
2,3-dihydroxypropanoic acid lactones (glyceric acid lactone);
2,3,4-trihydroxybutanoic acid lactones (stereoisomers: erythronolactone, threonolactone);
2,3,4,5-tetrahydroxypentanoic acid lactones (stereoisomers: ribonolactone, arabinolactone, xylonolactone, lyxonolactone);
2,3,4,5,6-pentahydroxyhexanoic acid lactones (stereoisomers: allonolactone, altronolactone, gluconolactone, mannolactone, gulonolactone, idonolactone, galactonolactone, talonolactone), and
2,3,4,5,6,7-hexahydroxyheptanoic acid lactones (stereoisomers: alloheptonolactone, altroheptonolactone, glucoheptonolactone, mannoheptonolactone, guloheptonolactone, idoheptonolactone, galactoheptonolactone, taloheptonolactone).

(b) Aldaric Acid Lactones

Aldaric acids are polyhydroxy dicarboxylic acids derived from an aldose by oxidation of both terminal carbon atoms to carboxyl groups, and the acid of which can be represented by the following general formula:

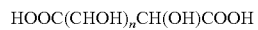

$$HOOC(CHOH)_nCH(OH)COOH$$

where n is an integer from 1 to 4.

The aldaric acids can exist as stereoisomers as D, L and DL or R, S and RS forms. The aldaric acids form intramolecular lactones by removing one mole of water between one carboxyl group and one hydroxyl group.

The following are representative aldaric acid lactones:
2,3-dihydroxybutane-1,4-dioic acid lactones
2,3,4-trihydroxypentane-1,5-dioic acid lactones (stereoisomers: ribarolactone, arabarolactone, xylarolactone, lyxarolactone);
2,3,4,5-tetrahydroxyhexane-1,6-dioic acid lactones (allarolactone, altrarolactone, glucarolactone, mannarolactone, gularic acid and gularolactone, idarolactone, galactarolactone, talarolactone);
2,3,4,5,6-pentahydroxyheptane-1,7-dioic acid lactones (stereoisomers: alloheptarolactone, altroheptarolactone, glucoheptarolactone, mannoheptarolactone, guloheptarolactone, idoheptarolactone, galactoheptarolactone, taloheptarolactone).

(c) Alduronic Acids

Alduronic acids are polyhydroxy acids resulting from oxidation of the alcohol group of an aldose to a carboxylic acid group, and can be represented by the following general formula:

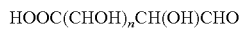
HOOC(CHOH)$_n$CH(OH)CHO where n is an integer from 1 to 4.

The alduronic acids can exist as stereoisomers as D, L and DL or R, S and RS forms. The alduronic acids form intramolecular lactones by removing one mole of water between the carboxyl group and one hydroxyl group.

The following are representative alduronic acid lactones: riburonolactone; araburonolactone; xyluronolactone; lyxuronolactone; alluronolactone; altruronolactone; glucuronolactone; mannuronolactone; guluronolactone; iduronolactone; galacturonolactone; taluronolactone; allohepturonolactone; altrohepturonolactone; glucohepturonolactone; mannohepturonolactone; gulohepturonolactone; idohepturonolactone; galactohepturonolactone and talohepturonolactone.

More preferably, component (i) is selected from gluconolactone, galactonolactone, glucuronolactone, galacturonolactone, gulonolactone, ribonolactone, saccharic acid lactone, pantoyllactone, glucoheptonolactone, mannonolactone, galactoheptonolactone, and mixtures thereof.

Most preferably, component (i) is selected from D-glucono-δ-lactone, D-glucono-γ-lactone, D-gluconic acid and mixtures thereof.

D-glucono-δ-lactone is the cyclic 1,5-intramolecular ester of D-gluconic acid, which is produced industrially by enzymatic oxidation of D-glucose.

D-glucono-δ-lactone per se is available in the form of a particulate solid (e.g. a crystalline powder). In aqueous media it may exist in an equilibrium mixture together with its isomer (D-glucono-γ-lactone), and its hydrolysis product (D-gluconic acid). Any of these forms or a mixture of any of these forms are suitable for use in the invention.

Most preferably D-glucono-δ-lactone per se is used as component (i) in the hair shaping composition of the invention.

In the hair shaping composition of the invention, the level of component (i) (preferably D-glucono-δ-lactone) preferably ranges from 0.5 to 6%, more preferably from 1 to 3% and most preferably from 1.5 to 2.5% by weight based on the total weight of the composition.

The hair shaping composition of the invention comprises, as component (ii), one or more aliphatic di- or tricarboxylic acids or salts or hydrates thereof.

Aliphatic di- or tricarboxylic acids for use in the invention typically have a molecular weight ($M_W$) ranging from 60 to 300 g/mol and at least one pK$_a$ value (measured at 25° C. in water) ranging from 2.5 to 4.

Illustrative examples of dicarboxylic acids for use in the invention correspond to the following general formula:

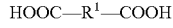
HOOC—R$^1$—COOH in which R$^1$ is a divalent, saturated or unsaturated, linear or branched hydrocarbyl radical having from 1 to 4 carbon atoms, and which may optionally be substituted with one or more hydroxyl groups.

Preferably R$^1$ is a divalent saturated linear alkyl radical of formula —[CH(X)]$_n$— in which n is an integer ranging from 1 to 3 and each X is independently selected from —H and —OH.

Specific examples of such dicarboxylic acids include malonic acid and tartaric acid.

Illustrative examples of tricarboxylic acids for use in the invention correspond to the following general formula:

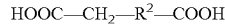
HOOC—CH$_2$—R$^2$—COOH in which R$^2$ is a divalent, saturated or unsaturated, linear or branched hydrocarbyl radical having from 1 to 3 carbon atoms, which is substituted with one —COOH group and which may optionally be substituted with one or more hydroxyl groups.

Specific examples of such tricarboxylic acids include citric acid, aconitic acid and tricarballylic acid.

Suitable salts include those with counterions such as alkali metal (preferably sodium), alkaline-earth metal (preferably calcium), ammonium and substituted ammonium ions.

Mixtures of any of the above-described aliphatic di- or tricarboxylic acids or salts or hydrates thereof may also be used.

More preferably component (ii) is selected from citric acid or salts or hydrates thereof, such as monosodium citrate, trisodium citrate, tricalcium citrate, trisodium citrate dihydrate, tripotassium citrate, monosodium citrate anhydrous, citric acid anhydrous, citric acid monohydrate and mixtures thereof.

Most preferably citric acid anhydrous and/or citric acid monohydrate is used as component (ii) in the hair shaping composition of the invention.

In the hair shaping composition of the invention, the level of component (ii) (preferably citric acid anhydrous and/or citric acid monohydrate) preferably ranges from 0.5 to 6%, more preferably from 1 to 3% and most preferably from 1.5 to 2.5% by weight based on the total weight of the composition.

The hair shaping composition of the invention comprises, as component (iii), glyoxylic acid or a salt or hydrate thereof.

Glyoxylic acid (OHC—COOH) is known to exist as a hydrate of formula (I) under certain conditions.

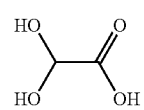

(I)

Also, glyoxylic acid may exist as a mixture of both the aldehyde and hydrate forms. The hydrate may also condense to dimers of formula (II).

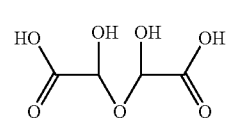

(II)

Glyoxylic acid also forms salts with counterions such as alkali metal (preferably sodium), alkaline-earth metal (preferably calcium), ammonium and substituted ammonium ions.

Any of these forms or a mixture of any of these forms are suitable for use in the invention.

Preferably glyoxylic acid in aqueous solution is used as component (iii) in the composition of the invention. Glyoxylic acid in aqueous solution generally exists as the hydrate of formula (I) together with a small proportion of the dimer of formula (II).

In the hair shaping composition of the invention, the level of component (iii) (preferably glyoxylic acid hydrate of formula (I)) preferably ranges from 0.1 to 8%, more preferably from 0.2 to 4% and most preferably from 0.5 to 2.5% by weight based on the total weight of the composition.

In the hair shaping composition of the invention, the weight ratio of component (i) (preferably D-glucono-δ-lactone) to component (iii) (preferably glyoxylic acid hydrate of formula (I)) preferably ranges from about 8:1 to about 3:5, and more preferably ranges from about 5:1 to about 1:1.

In the hair shaping composition of the invention, the weight ratio of component (ii) (preferably citric acid anhydrous and/or citric acid monohydrate) to component (iii) (preferably glyoxylic acid hydrate of formula (I)) preferably ranges from about 8:1 to about 3:5, and more preferably ranges from about 5:1 to about 1:1.

Advantageously, the hair shaping composition of the invention does not require the incorporation of reducing agents, and a hair shaping composition according to the invention is generally substantially free of such materials.

The term "substantially free" in the context of this invention means that reducing agents are absent or included in trace quantities only, such as no more than 0.1%, preferably no more than 0.01%, and more preferably from 0 to 0.001% by weight based on the total weight of the composition.

The term "reducing agent" in the context of this invention means an agent which is effective to break hair disulfide bonds when applied to hair for a period ranging from about 3 to 15 minutes and at a temperature ranging from about 20 to 30° C. Examples of such reducing agents are ammonium thioglycolate (in a solution having a pH of between about 7 and 10.5), glyceryl monothioglycolate (employed at a pH of less than 7), thioglycolic acid, dithioglycolic acid, mercaptoethyl amine, mercaptopropionic acid, dithioglycolate and alkali metal or ammonium sulfites or bisulfites.

A hair shaping composition according to the invention may suitably have a conditioning gel phase, which may be generally characterized as a gel (Lβ) surfactant mesophase consisting of surfactant bilayers. Such a conditioning gel phase may be formed from a cationic surfactant, a high melting point fatty alcohol and an aqueous carrier. Typically these components are heated to form a mixture, which is cooled under shear to room temperature. The mixture undergoes a number of phase transitions during cooling, normally resulting in a gel (L$_β$) surfactant mesophase consisting of surfactant bilayers.

Examples of suitable cationic surfactants which are useful for forming the conditioning gel phase include quaternary ammonium cationic surfactants corresponding to the following general formula:

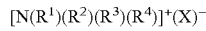

[N(R$^1$)(R$^2$)(R$^3$)(R$^4$)]$^+$(X)$^-$ in which R$^1$, R$^2$, R$^3$, and R$^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, R$^1$ is a C$_{16}$ to C$_{22}$ saturated or unsaturated, preferably saturated, alkyl chain and R$^2$, R$^3$ and R$^4$ are each independently selected from CH$_3$ and CH$_2$CH$_2$OH, preferably CH$_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10%, preferably from 0.2 to 5% and more preferably from 0.25 to 4% (by total weight of cationic surfactant based on the total weight of the composition).

By "high melting point" in the context of this invention is generally meant a melting point of 25° C. or higher. Generally the melting point ranges from 25° C. up to 90° C., preferably from 40° C. up to 70° C. and more preferably from 50° C. up to about 65° C.

The high melting point fatty alcohol can be used as a single compound or as a blend or mixture of at least two high melting point fatty alcohols. When a blend or mixture of fatty alcohols is used, the melting point means the melting point of the blend or mixture.

Suitable fatty alcohols of this type have the general formula R—OH, where R is an aliphatic carbon chain. Preferably R is a saturated aliphatic carbon chain comprising from 8 to 30 carbon atoms, more preferably from 14 to 30 carbon atoms and most preferably from 16 to 22 carbon atoms.

R can contain, in addition to carbon and hydrogen atoms, ether linkages, and other groups such as amino groups.

Most preferably, the fatty alcohol has the general formula CH$_3$(CH$_2$)$_n$ OH, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty alcohols may also be suitable.

The level of fatty alcohol suitably ranges from 0.01 to 10%, preferably from 0.1 to 8%, more preferably from 0.2 to 7% and most preferably from 0.3 to 6% (by weight based on the total weight of the composition).

The weight ratio of cationic surfactant to fatty alcohol is suitably from 1:1 to 1:10, preferably from 1:1.5 to 1:8, optimally from 1:2 to 1:5.

A hair shaping composition according to the invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

The pH of the hair shaping composition of the invention is 4 or less, and preferably ranges from 1.5 to 3.8, more preferably from 2.5 to 3.5 and most preferably from 2.8 to 3.2.

Preferably, the hair shaping composition is a single dose composition. The term "single dose" in the context of this invention means that the composition is to be topically applied to the hair in one go.

The hair shaping composition of the invention is suitable for topical application to hair for improved hair volume-down. The term "volume-down" in the context of this invention generally means reduced visible bulkiness of the hair. For many consumers, improved hair volume-down provides a number of associated benefits, such as improved straightness, smoothness, manageability and style retention.

The hair shaping composition of the invention is preferably topically applied to the hair at a temperature from 15 to 40° C., and more preferably at a temperature from 20 to 30° C.

Preferably, the composition is applied to dry hair. The term "dry hair" in the context of this invention generally means hair from which free water (i.e. water disposed as a film or droplets on the cuticle surface) has been substantially removed. Hair may be dried by exposure to air, by use of a heated hair drying appliance, by rubbing with a water-absorbent article, or by a combination of any of these methods. Preferably, the dry hair will not have been washed or actively wetted, (such as by shampooing, conditioning, rinsing or otherwise treating with an aqueous composition) in the preceding 2 hours and more preferably in the preceding 3 hours prior to topical application of the composition, and will have been permitted to acclimatise to atmospheric conditions. In such circumstances there is substantially no free water present which interferes with the adsorption of the composition on application. A suitable indicator of dry hair in the context of this invention would be a hair fibre whose calculated water content does not exceed 25% by weight based on the total weight of the hair fibre.

After topical application to the hair, it is preferred that the hair shaping composition is allowed to remain in contact with the hair without rinsing. More preferably, the hair shaping composition is allowed to remain in contact with the hair without rinsing until the hair thus treated is dry.

The hair thus treated may be dried naturally by exposure to air, by use of a heated hair drying appliance, by rubbing with a water-absorbent article, or by a combination of any of these methods.

The hair shaping composition may thus remain in contact with the hair after topical application for a period of at least about 3 minutes up to 3 hours or more if the hair is allowed to dry naturally.

In step (ii) of the method of the invention, the treated hair is mechanically shaped.

Mechanical shaping of the hair in the method of the invention can be accomplished by such means as the finger tips, a plastic hair pick or the tail of a comb, the shaping being performed on portions of the hair comprising strands of hair in various numbers. Using such means the hair may be pulled, combed, smoothed, pressed or flattened into a straightened configuration; or shaped gently into bends, waves or curls.

Preferably in step (ii) of the method of the invention, the hair is mechanically shaped by mechanically straightening it. For example, the hair may be pulled, combed, smoothed, pressed or flattened into a straightened configuration.

A hot tool, such as an electrically heated flat hair iron or hand-held hair dryer, may be used in the mechanical shaping step. Such tools apply high levels of heat directly to the hair, and are usually employed at temperature settings of at least 50° C., with an upper limit dependent on the particular tool.

Preferably the hair is mechanically shaped in step (ii) of the method of the invention by mechanically straightening it with an electrically heated flat hair iron. Electrically heated flat hair irons are usually employed at a temperature of at least 120° C. and can reach temperatures as high as 230° C.

However, the method of this invention also gives good results at significantly lower operating temperatures than this (e.g. from around 170 to 200° C., or even from around 170 to 185° C.). This is particularly advantageous for minimizing damage to hair.

In a typical method for shaping hair according to the invention, the hair shaping composition is topically applied to dry hair and the hair thus treated is combed straight at a temperature from 15 to 40° C., preferably at a temperature from 20 to 30° C. The treated, combed hair is dried (or allowed to dry) without rinsing the composition from the hair, and the dry hair is then mechanically shaped by mechanically straightening it with a hot tool (preferably an electrically heated flat hair iron) at an operating temperature from 120 to 220° C., preferably from 150 to 210° C., and more preferably from 170 to 200° C.

The hair shaping composition may then be rinsed from the hair at the next wash.

Surprisingly, the inventors have found that the improved "volume-down" provided by the hair shaping composition in accordance with the invention is capable of persisting after washing.

Accordingly the invention also provides a method for shaping and re-shaping hair comprising the following steps:
(i) treating the hair by topical application of a hair shaping composition as defined above;
(ii) mechanically shaping the treated hair;
(iii) rinsing the shaped hair, and
(iv) mechanically re-shaping the rinsed hair.

In a typical method for shaping and re-shaping hair according to the invention, the hair shaping composition is topically applied to dry hair and the hair thus treated is combed straight at a temperature from 15 to 40° C., preferably at a temperature from 20 to 30° C. The treated, combed hair is dried (or allowed to dry) without rinsing the composition from the hair, and the dry hair is then mechanically straightened with a hot tool at an operating temperature from 120 to 220° C., preferably from 150 to 210° C., and more preferably from 170 to 200° C. The hair shaping composition is then rinsed from the hair at the next wash: typically after a period of about 24 to 72 hours following the initial application of the composition in step (i). The rinsed hair is then mechanically re-shaped.

The rinsing step may be conducted with water alone or with shampoo.

The use of hot tools is not essential in the re-shaping step. This is especially advantageous for consumers who wish to reduce or avoid the exposure of their hair to high temperatures, for example if their hair is fragile or overprocessed from previous chemical treatments such as bleaching and perming.

Accordingly the hair is preferably re-shaped by combing it into a straightened configuration at a temperature from 15 to 40° C., more preferably at a temperature from 20 to 30° C.

Method steps (i) to (iv) as described above may also be repeated over one or more (e.g. two or three) cycles.

The invention is further illustrated with reference to the following, non-limiting Examples.

In the Examples, all ingredients are expressed by weight percent of the total formulation, and as level of active ingredient. Comparative Examples (not according to the invention) are indicated by letter; Examples according to the invention are indicated by number.

EXAMPLES

Example 1 and (Comparative) Examples A and B

Dark brown European wavy#6 switches of length 25 cm and weight 2 gms, were soaked in the following test solutions:
Example A: Aqueous solution, 2% glyoxylic acid
Example B Aqueous solution, 2% citric acid and 2% D-glucono-δ-lactone
Example 1: Aqueous solution, 2% glyoxylic acid, 2% citric acid and 2% D-glucono-δ-lactone Control switches were soaked in water.

After 30 minutes, the switches were removed and were left to dry at 20 C and 50% RH.

When dry the switches were straightened with GHD irons (5 passes). These have an operating temperature below 200° C. (typically between 175 and 185° C.).

The switches were subsequently washed a number of times and images of the switches were captured when dry and after combing.

The volumes of the switches were measured using an image analysis kit. The volume of the switches shows the volume-down (straightness) benefits of the treatment (here volume refers to the projection of the switch image on to the screen and is given in $mm^2$). The percentage benefit (i.e. decrease in volume) with respect to control (water) was also measured.

The results are shown in Table 1.

TABLE 1

Volumes of treated hair switches in $mm^2$ after a single heat treatment and subsequent three washes.

| | Treatment | | | | | |
|---|---|---|---|---|---|---|
| | after 1st wash | | after 2nd wash | | after 3rd wash | |
| | volume | % benefit | volume | % benefit | volume | % benefit |
| Control (water) | 18142 | 0.0 | 17309 | 0.0 | 17392 | 0.0 |
| Example A | 11884 | 34.5 | 12929 | 25.3 | 14795 | 14.9 |
| Example B | 12555 | 30.8 | 11003 | 36.4 | 12163 | 30.1 |
| Example 1 | 8888 | 51.0 | 8404 | 51.4 | 8062 | 53.6 |

From the table it can be seen that the composition of Example 1 provides a much better straightening benefit than either Example A or Example B. Also the switches treated with Example 1 maintain their straightness after multiple washes. By contrast, the straightness of the switches treated with either Example A or Example B tapers off after the $2^{nd}$ and $3^{rd}$ washes respectively.

Furthermore, it can be seen from a comparison of the results that the composition according to the invention provides a synergistic straightening benefit after the 3rd wash.

Example 2

The following formulation illustrates a hair shaping composition according to the invention

| Ingredient | % activity | % w/w raw material |
|---|---|---|
| Behentrimonium chloride | 70 | 1.1429 |
| Cetearyl alcohol | 100 | 3.0 |
| Perfume | 100 | 0.60 |
| Preservative | 100 | 0.2 |
| Dimethicone emulsion | 70 | 1.429 |
| Citric Acid | 100 | 2.0 |
| Glyoxylic Acid | 50 | 2.0 |
| D-glucono-δ-lactone | 100 | 2.0 |
| Water | 100 | To 100% | pH = 3.0

The invention claimed is:

1. A hair shaping composition suitable for topical application to hair, the composition having a pH of 4 or less and comprising, in an aqueous continuous phase:
   (i) at least 0.5% (by weight based on the total weight of the composition) of one or more polyhydroxy acid lactones;
   (ii) at least 0.5% (by weight based on the total weight of the composition) of one or more aliphatic di- or tricarboxylic acids, and
   (iii) at least 0.1% (by weight based on the total weight of the composition) of glyoxylic acid or a salt or hydrate thereof.

2. A composition according to claim 1, in which the level of component (i) ranges from 1.5 to 2.5% by weight based on the total weight of the composition.

3. A composition according to claim 1, in which component (i) is D-glucono-δ-lactone.

4. A composition according to claim 1, in which the level of component (ii) ranges from 1.5 to 2.5% by weight based on the total weight of the composition.

5. A composition according to a claim 1, in which component (ii) is citric acid anhydrous and/or citric acid monohydrate.

6. A composition according to claim 1, in which the level of component (iii) ranges from 0.5 to 2.5% by weight based on the total weight of the composition.

7. A composition according to claim 1, in which component (iii) is glyoxylic acid hydrate.

8. A method for shaping hair which comprises the steps of treating the hair by topical application of a hair shaping composition according to claim 1, followed by mechanically shaping the treated hair.

9. A method according to claim 8, in which the treated hair is mechanically shaped by mechanically straightening it with a hot tool at an operating temperature from 170 to 200° C.

10. A method according to claim 1, in which the hair shaping composition is topically applied to dry hair.

11. A method for shaping and re-shaping hair comprising the following steps:
   (i) treating the hair by topical application of a hair shaping composition according to claim 1,
   (ii) mechanically shaping the treated hair;
   (iii) rinsing the shaped hair, and
   (iv) mechanically re-shaping the rinsed hair.

* * * * *